(12) United States Patent
Bowman et al.

(10) Patent No.: US 6,372,245 B1
(45) Date of Patent: Apr. 16, 2002

(54) PLASTICIZED BIOERODIBLE CONTROLLED DELIVERY SYSTEM

(75) Inventors: Lyle M. Bowman, Pleasanton; Santosh Kumar Chandrasekaran, Moraga; Rajesh Patel, San Mateo; Hoa Vinh Vo, Alameda, all of CA (US)

(73) Assignee: Insite Vision Incorporated, Alameda, CA (US)

( * ) Notice: Subject to any disclaimer, the term of this patent is extended or adjusted under 35 U.S.C. 154(b) by 0 days.

(21) Appl. No.: 08/233,211

(22) Filed: Apr. 22, 1994

Related U.S. Application Data

(63) Continuation of application No. 07/997,914, filed on Dec. 29, 1992, now abandoned.

(51) Int. Cl.$^7$ ................................................. A61K 9/10
(52) U.S. Cl. ........................ 424/427; 424/428; 424/400; 514/912
(58) Field of Search ................................. 424/426, 400, 424/427–428, 484–488, 49; 514/912–915

(56) References Cited

U.S. PATENT DOCUMENTS

| | | | |
|---|---|---|---|
| 4,138,344 A | 2/1979 | Choi et al. | |
| 4,179,497 A | 12/1979 | Cohen et al. | 424/22 |
| 4,343,787 A | 8/1982 | Katz | 424/78 |
| 4,865,846 A | * 9/1989 | Kaufman | 424/428 |

FOREIGN PATENT DOCUMENTS

| | | |
|---|---|---|
| EP | 0 077 261 | 4/1983 |
| FR | 2 299 356 | 8/1976 |
| FR | 2583056 | 12/1986 |

OTHER PUBLICATIONS

"Effect of Hydrophilicity on the Hydrolysis of Poly(Ortho ester)s", C. Smith, Proceed. Intern. Symp. Control Rel. Bioact. Mater, 19 (1992), Controlled Release Society, Inc., pp. 48–49.

"The Use of Poly (Ortho Esters) In the Treatment of Cancer And In the Pulsed Release of Proteins", J. Heller, K.V. Roskos, S.Y. Ng, P. Wuthrich, R. Duncan and L.W. Seymour, Proceed. Intern, Symp. Control. Rel. Bioact. Mater., 19(1992), Controlled Release Society, Inc., pp. 128–131.

"Biodegradable Polyester Hydrogels: The Role of Water", C.G. Pitt, S.S. Shah, K.J.,Zhu, and Y. Cha, Proceed. Intern. Symp. Control. Rel. Bioact. Mater., 19(1992), Controlled Release Society, Inc., p. 130.

"Albumin–Heparin Microspheres For The Controlled Delivery of Drugs", J. Feijen, H.F.M. Cremers, G. Kwon, Y.H. Bae., S.W. Kim, R. Verrijk, A.C. Begg, H.P.J.M. Noteborn, J.G. McVie, R. Wolf, E.H. Blaauw, K. Lam, J.M. Schakenraad, Proceed. Intern. Symp. Control. Rel. Bioact. Mater., 19(1992), Controlled Release Society, Inc., pp. 131–132.

* cited by examiner

*Primary Examiner*—Edward J. Webman
(74) *Attorney, Agent, or Firm*—Arnold & Porter

(57) ABSTRACT

A controlled release medicament delivery system comprises a plasticized bioerodible polymer, such as a polyorthoester. Medicament desirably is entrapped in the plasticized polymer. The resulting delivery system is able to release the medicament in a controlled and sustained manner. The formulation is particularly advantageous for use as a once-a-day eyedrop. During preparation, the polymer may be heated to an elevated temperature for a sufficient time to substantially reduce its molecular weight.

40 Claims, No Drawings

PLASTICIZED BIOERODIBLE CONTROLLED DELIVERY SYSTEM

RELATED APPLICATIONS

This application is a continuation of application Ser. No. 07/997,914, filed on Dec. 29, 1992 now abandoned.

The present application is related to a copending application Ser. No. 07/997,913 entitled Bioerodible Controlled Delivery System, filed on the same date as the present application. Systems of the present invention can be used as one component of the system described in the above-identified application.

FIELD OF THE INVENTION

The present invention is concerned with sustained release delivery systems for medicaments, especially topical ophthalmic delivery systems, More particularly, the present invention relates to a sustained release drug delivery system based on a flowable, plasticized bioerodible polymeric matrix material.

BACKGROUND

In topical administration of medicaments to the eye, a variety of factors can be important, among them: comfort, consistency and accuracy of dosage, type and time of any vision interference, ease of administration, and timing of delivery. Prior ophthalmic delivery vehicles have suffered drawbacks in one or more of those areas.

For example, eyedrops in the form of aqueous solutions or suspensions can be rapidly washed away by the eye's tear fluid. Ointments or creams can blur the vision and oftentimes can result in other undesirable side effects. Gelatin lamellae or other films or sheets, ocular inserts and non-aqueous suspensions and emulsions all can cause immediate pain and continuing discomfort and can also interfere with vision. A number of drug delivery systems or formulations have been developed in an attempt to ameliorate or to avoid the foregoing problems.

One group of polymers found useful in the eye are disclosed in Choi et al, U.S. Pat. No. 4,138,344, issued Feb. 6, 1979. In particular, Choi et al disclose orthoester and orthocarbonate polymers having a repeating mer comprising a hydrocarbon radical and a symmetrical dioxycarbon unit. The polymers are generally highly viscous or solid and have been prepared for use in the form of a bioerodible insert encapsulated by another polymer.

The bioerodible ocular insert of Choi et al consists of a bioerodible polymer comprising a continuous matrix in which particles of drug are dispersed. When the ocular insert is placed in the environment of the eye, the polymer gradually bioerodes and releases drug to the eye and surrounding tissues. Until now, it is believed that the polymers have been suitable for administration to the eye only as an insert because of their tackiness and poor handling ability.

The present invention, which is based on a flowable, plasticized, bioerodible polymeric matrix material, evolved from efforts to obtain sustained release benefits from such polymers without constraints and disadvantages associated with inserts. It is believed that before the present invention, very small amounts of polyethylene glycol were added to a Choi et al. material for a different purpose, i.e., in an attempt to combat its tackiness while still maintaining it as a solid.

OBJECTS AND SUMMARY

It is an object of the present invention to provide novel sustained release delivery systems.

It is a particular object of this invention to provide novel sustained release delivery systems for topical ophthalmic delivery of medicaments.

A further object of this invention is to provide novel, sustained release, topical ophthalmic delivery systems suitable for administration of medicaments at intervals of once daily or even longer.

Yet another object of this invention is to provide a method for convenient therapeutic treatment using a delivery system which has a prolonged release time for medicaments.

A still further object of this invention is to provide novel methods for the preparation of sustained release delivery systems.

In accordance with a preferred form of the invention intended to accomplish at least some of the foregoing objects, a sustained release medicament delivery system comprises, and more preferably consists essentially of, a plasticized, bioerodible polymer for carrying medicament.

When formulated as a topical ophthalmic delivery system, the viscosity of the composition is desirably in a range suitable for administration to the eye in ribbon form or in drop form. Preferably that viscosity is from about 1,000 to about 55,000 cps. For drops the viscosity is more preferably from about 5,000 to about 30,000 cps, and for administration in ribbon form the viscosity is more preferably from about 40,000 to about 55,000 cps. There can, however, be overlap in the drop and ribbon viscosity ranges by reason of variations in formulation techniques and ingredients. When formulated for injection, the viscosity of the injectable liquid can be substantially greater than 100,000 cps, but still preferably such that the liquid can be passed through an 18 gauge or smaller needle at room temperature (about 20 °C.).

The delivery system comprises a plasticized bioerodible polymer. As used herein "erodible" and "bioerodible" refer to the property of the polymer to break down as a unit structure by chemical decomposition, as opposed to physical degradation, e.g., by the polymer reacting with water or through polymer reaction with enzymes, water in tear fluids or other biological materials. Preferably, however the bioerodible polymer is a polyorthoester.

Preferred plasticizers are, polyethylene glycol, glycerin (glycerol), propylene glycol, polypropylene glycol, ethylene glycol, cetyl alcohol and polyvinyl alcohol. In topical ophthalmic preparations only small amounts of ethylene glycol should be used because of potential toxicity in the eye.

The plasticizers are preferably present in systems of the present invention in an amount from about 5% to about 70% of the total weight of the bioerodible polymer and plasticizer (excluding medicament), more preferably about 5% to about 40% and for some formulations preferably about 10% to about 30% by weight. In any event, the amount of plasticizer or any other constituent is such that the system is flowable and remains essentially bioerodible.

The bioerodible polymeric material is preferably selected from the group consisting of polysaccharides, proteinaceous polymers and their soluble derivatives, polypeptides, polyesters, polylactic acid polymers, polyglycolic acid polymers, poly(lactic/glycolic) copolymers and polyorthoesters. The most preferred materials are plasticized and unplasticized polyorthoesters, especially poly(2,2 dioxo-trans-1,4 cyclohexane dimethylene tetrahydrofuran), of the type disclosed by Choi et al, U.S. Pat. No. 4,128,344 which is hereby incorporated by reference.

The flowable bioerodible material of the delivery system is preferably present in an amount within a range of about 30% to about 95%, by weight based on the total weight of the bioerodible polymer and plasticizer (excluding medicament), more preferably about 60% to about 95%, by weight of the bioerodible polymer and plasticizer (excluding medicament).

Where topical ophthalmic compositions useful to ameliorate "dry eye" conditions are formulated, the medicament, as that term is here used, may be a demulcent. Of course, the term medicament also includes, and in most instances will be constituted by, what are often referred to a over the counter or prescription drugs. Drugs administered by means of the controlled release drug delivery systems of the present invention preferably include an adrenocorticotrophic hormone, insulin, vitamin, steroid, narcotic antagonist, antibiotic, anticancer drug, antihypotensive drug, aminosteriod or protein. The drugs may be in either the free base or the acid form. Particular advantages are perceived for administering water soluble drugs inasmuch as they are believed less likely to diffuse out of the system. Therefore, their administration is more erosion controlled.

The present invention also includes a process for making a sustained release medicament system which comprises the steps of mixing a plasticizer with the bioerodible polymer at a temperature and time sufficient to form a substantially homogenous mixture at room temperature. The time and temperature of mixing will depend on factors such as molecular weight of the polymer, viscosity, and temperature stability of the components. The medicament is added to the mixture with mixing at a temperature compatible with the stability of the material.

Depending on its molecular weight, the bioerodible polymer employed can be at room temperature a tacky, solid or semi-solid substance, or a tacky, extremely viscous liquid. In order to enhance the flowability and the homogeneity of the system, the bioerodible polymer is heated, together with plasticizer. Plasticizing can reduce or minimize the need for heat that might adversely affect the stability of the medicament. Plasticizing also may reduce the tackiness of the polymer.

It can be particularly desirable with higher molecular weight forms of the preferred poly(2,2-dioxo-trans-1,4-cyclohexane dimethylene tetrahydrofuran) polymer to heat the polymer at an elevated temperature for a time sufficient to substantially reduce its molecular weight. Heating to a temperature range of about 140° C. to about 180° C. for 30 minutes to ten days is recommended to advantageously reduce the polymer molecular weight. The system is then cooled to room temperature. Alternatively, a low molecular weight polymer may be used.

In order to minimize the potential for irritation (e.g. eye irritation) as a result of byproducts produced during molecular weight reduction (e.g. decomposition products such as gamma-butyrolactone and cyclohexanyl-dimethanol, when the preferred polyorthoesters are employed), it can be advantageous to pull a vacuum during heating to remove such byproducts, especially those byproducts whose vapor pressure is sufficiently high to be amenable.

Addition of the medicament can be accomplished in a variety of ways. One way is to mix the medicament with the bioerodible polymer, in an induced, flowable condition, prior to adding the plasticizer. The bioerodible polymer may be placed in that flowable condition by heating.

It is preferred, however, to add the medicament during or after plasticizing. The timing, however, of that addition should be determined with consideration given to the heat sensitivity of the medicament, which might be unstable at some elevated temperatures, or when heated for longer times.

In such circumstances, it can be advantageous to first heat and actively mix the bioerodible polymer and the plasticizer, and then to add the medicament, preferably again with active mixing, either during cooldown or during a reheat step under less severe temperature or time conditions.

It is also possible to prepare the formulation by dissolving the bioerodible polymer and the medicament in a suitable solvent for both of them. The solvent is then stripped off in any suitable manner (for example, by heating or pulling a vacuum), leaving the medicament suspended in the polymer. The solvent should be non-toxic to the desired target tissue and easily removable. It should also be essentially free of water. A suitable solvent for poly (2,2 dioxo-trans-1,4 cyclohexane dimethylene tetrahydrofuran) is ethanol. Other suitable solvents such as other alcoholic solvents, tetrahydrofuran, methylene chloride, or the like may also be employed alone or in combination.

In preparing some "dry eye" formulations according to the present invention, separate demulcents may be added as medicament. However, it is also contemplated that some plasticizers, such as polyethylene glycol, employed to reduce viscosity of the bioerodible polymer can themselves constitute medicament, by acting as a lubricant carried by the bioerodible material.

In accordance with further aspects of the present invention there is thus provided a therapeutic treatment with a delivery system having sustained integrity and a prolonged release time for medicament. A flowable delivery system is formulated with the plasticized essentially bioerodible polymer carrying the medicament. The flowable system carrying medicament is delivered to a mammalian organism in need of treatment by the medicament, and medicament release is controlled by bioerosion of the polymer.

In a topical ophthalmic treatment, the viscosity of the system is adjusted so as to be suitable for administration to the eye in ribbon or drop form, and controlled release of medicament to the eye preferably can take place over a prolonged time, even a period of twenty-four hours or longer. The system may also be formulated as a liquid which is injected into the mammalian organism through an 18 guage or smaller needle.

Oral formulations, particularly in the form of viscous liquids or as capsules which carry medicament-containing delivery systems of the present invention are also contemplated.

Other objects, advantages and aspects of the present invention will become apparent from the detailed description below.

DETAILED DESCRIPTION

A wide variety of bioerodible polymers are contemplated as useful in preparing controlled drug delivery systems according to the present invention. The below mentioned bioerodible polymers are believed particularly suited for the methods and compositions of the present invention by reason of their characteristically low human toxicity and virtually complete biodegradability. Of course, it will be understood that any bioerodible polymer may be useful in the practice of the present invention in its broadest form as long as it can be plasticized to flowable condition at room temperature, is non-toxic and can be degraded by chemical decomposition through contact with body fluids. Further, different molecular weights of polymers may be used in the practice of the present invention as long as the appropriate controlled release feature of the formulation as a result of bioerosion is maintained.

Polymers useful in the present invention may be derived from a variety of sources and should be formulated to be or behave as a bioerodible polymer in the sense that they biodegrade by reaction with water, enzymes or other biological materials encountered upon administration to the body of a mammalian organism. Such polymers include polysaccharides, proteinaceous polymers and their soluble derivatives, polypeptides, polyesters, polylactic acid polymers, polyglycolic acid polymers, poly(lactide/glycolide) copolymers, polyorthoesters, and the like.

The polysaccharides may be poly-1,4-glucans, e.g., starch glycogen, amylose and amylopectin, and the like. Preferably, such a bioerodible polymer is a water-soluble derivative of a poly-1,4-glucan, including hydrolyzed amylopectin, hydroxyalkyl derivatives of hydrolyzed amylopectin such as hydroxyethyl starch, hydroxyethyl amylose, dialdehyde starch, and the like.

Proteinaceous polymers and their soluble derivatives include gelatin, biodegradable synthetic polypeptides, elastin, alkylated collagen, alkylated elastin, and the like.

Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-leucine, L-valine, L-tyrosine, and the like.

Definitions or further descriptions of any of the foregoing polymers are well known in the art and may be found by referring to any standard biochemistry reference text such as "Biochemistry" by Albert L. Lehninger, Worth Publishers, Inc. and "Biochemistry" by Lubert Stryer, W. H. Freeman and Company, both of which are hereby incorporated by reference.

Polyorthoesters are preferred in the practice of the present invention. Those polymers are normally a highly viscous, tacky substance at low molecular weight, and a rigid, tacky solid at high molecular weight. Choi et al, U.S. Pat. No. 4,138,344 issued Feb. 6, 1979, which is incorporated herein by reference in its entirety, describes polyorthoesters comprising hydrocarbon radicals and a symmetrical dioxycarbon unit with a multiplicity of organic groups bonded thereto. In particular, Choi, et al discloses polymers comprising a carbon-oxygen backbone having a dioxycarbon moiety with a plurality of organic groups pendant from the dioxycarbon, The polymers are represented by the following general formula:

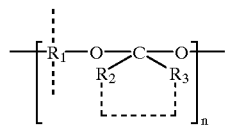

wherein $R_1$ is a di, tri or tetravalent alkylene, alkenylene, alkyleneoxy, cycloalkylene, cycloalkylene substituted with an alkyl, alkoxy or alkenyl, cycloalkenylene, cycloalkenylene substituted with an alkyl, alkoxy, alkenyloxy, alkylene, alkenylene, alkyleneoxy, alkenyleneoxy, alkylenedioxy, alkenylenedioxy, aryloxy, aralkyleneoxy, aralkenyleneoxy, aralkylene dioxy, aralkenylenedioxy, oxa, or $OR_1O$ with $R_1$ defined as above; and wherein, a) $R_1$ is divalent when $R_2$ and $R_3$ are alkyl, alkenyl, alkoxy, or alkenyloxy, with at least one of $R_2$ or $R_3$ an alkoxy or alkenyloxy; b) $R_1$ is divalent when $R_2$ and $R_3$ are intramolecularly covalently bonded to each other and to the same dioxycarbon atom to form a heterocyclic ring or a heterocyclic ring substituted with an alkyl, alkoxy or alkenyl when $R_2$ is an alkyleneoxy or alkenyleneoxy and $R_3$ is an alkyleneoxy, alkenyleneoxy or alkylene; c) $R_1$ is divalent when $R_2$ and $R_3$ are intramolecularly covalently bonded to each other and to the same dioxy carbon atom to form a fused polycyclic ring or a fused polycyclic ring substituted with an alkyl, alkoxy or alkenyl when $R_2$ is an oxa, alkyleneoxy or alkenyleneoxy and $R_3$ is aryloxy, aralkyleneoxy, aralkenyleneoxy or aralkylene; d) $R_1$ is divalent when $R_2$ or $R_3$ is an $OR_1O$ bridge between polymer backbones bonded through their dioxycarbon moieties, and the other $R_2$ or $R_3$ is an alkyl, alkenyl, alkyloxy, or alkenyloxy; e) $R_1$ is tri or tetravalent when $R_2$ and $R_3$ are covalently bonded to each other and to the same dioxycarbon atom to form a heterocyclic ring or a heterocyclic ring substituted with an alkyl, alkoxy or alkenyl when $R_2$ is an alkyleneoxy or alkenyleneoxy and $R_3$ is an alkyleneoxy, or alkylene; and f) $R_1$ is tri or tetravalent when $R_2$ and $R_3$ are covalently bonded to each other and to the same dioxy carbon atom to form a fused polycyclic ring or fused polycyclic ring substituted with an alkyl, alkoxy or alkenyl when $R_2$ is an oxa, alkyleneoxy or alkenyleneoxy and $R_3$ is aryloxy, aralkyleneoxy, aralkenyleneoxy or aralkylene.

The polymers contemplated as useful in the practice of the present invention include homopolymers, copolymers of the random and block types formed by reacting monomers or mixtures of preformed homopolymers and/or copolymers, branched polymers and cross-linked polymers. In addition, thermoplastic line polymer; when $R_1$ is divalent, $R_2$ and $R_3$ are substituted with a non-crosslinking group or are bonded intramolecularly, thermosetting cross-linked polymers when $R_1$ is divalent and $R_2$ or $R_3$ is intermolecularly bonded between different polymeric backbones; and, thermosetting cross-linked polymers when $R_1$ is tri or tetravalent and $R_2$ and $R_3$ are substituted wit non-crosslinking groups, or bonded intramolecularly, are useful.

The phrase hydrocarbon radical appearing above and as used elsewhere in the specification, includes, for the purpose of this invention, the terms embraced by $R_1$, $R_2$ and $R_3$ as defined below.

The term alkylene used in this specification for $R_1$ denotes a straight or branched chain divalent, trivalent or tetravalent alkylene radical of 1 to 10 carbon atoms inclusive such as 1,2-ethylene; 1,3-propylene; 1,2-propylene; 1,4-butylene; 1,5-pentylene 1,6-hexylene, 1,2,5-hexylene; 1,3,6-hexylene; 1,7-heptylene; 2-methyl-1,7-heptylene; 1,8-octylene; 1,10-decylene; 2-propyl-1,6-hexylene; 1,1-dimethyl-1,6-hexylene; and the like. These alkylene chains are derived from the corresponding glycols.

The term alkenylene used for $R_1$ denotes an unsaturated straight or branched chain multivalent radical having 2 to 10 carbon atoms such as 1,4-but-2-enylene: 1,6-hex-3-enylene; 1,7-hept-3-enylene; 1,8-oct-3-enylene; 1,9-non-3-enylene; 4-propyl-(1,6-hex-3-enylene); 5-methoxy-(1,6-hex-3-enylene); 2-propenyl-(1,6-hex-3-enylene); and the like.

The term cycloalkylene as used for $R_1$ includes monocyclic, lower cycloalkylene radicals of 3 to 7 carbons such as cyclopropylene: cyclobutylene; cyclopentylene; cyclohexylene and cycloheptylene. Similarly, the phrase cycloalkylene substituted with an alkyl of 1 to 7 carbons, an alkoxy of $_1$ to 7 carbons, or an alkenyl of 2 to 7 carbons, includes substituted cycloalkylenes such as 2 -methyl-1,3-cyclopropylene; 2-methyl-1,4-cyclopentylene; 2-methyl-1, 6-cyclohexylene; 2-ethoxy-2,3-cyclopentylene; 2-methyl-1, 6-cyclohexylene; 2-ethoxy-2,3-cyclopropylene; 5-butoxy-1,4-cyclopentylene; 2-methoxy- 1,4-cyclohexylene;

2-propenyl- 1,5-cyclopentylene; 2-isobutenyl-1,6-cyclohexylene; and the like.

Exemplary $R_1$ cycloalkenylene and $R_1$ cycloalkenylene substituted with an alkyl of 1 to 7 carbons, an alkoxy of 1 to 7 carbons, or an alkenyl of 2 to 7 carbons, include monocyclic alkylenes having from 4 to 7 carbons as ring members, such as 1,4-cyclopent-2-enylene; 1,5-cyclopent-3-enylene; 1,6-cyclohex-2-enylene; 1,6-cyclohex-2-enylene and the substituted rings such as 5-methyl-(1,4-cyclopent-2-enylene); 6-ethyl-(1,4-cyclohex-2-enylene); 6-ethoxy-(1,5-cyclohex-2-enylene); 2-propyl-(1,5-cyclohex-3-enylene); 2-methoxy-(1,4-cyclohex-2-enylene); 2-methoxy-(1,4-cyclohept-2-enylene), and the like.

The expressions $R_1$ arylene and $R_1$ arylene substituted with an alkyl of 1 to 7 carbons, an alkenyl of 2 to 7 carbons, or an alkoxy of 1 to 7 carbons, include the benzenoid groups such as phenylene, phenylalkylene and phenylalkenylene. Typical groups are 1,4-phenylene; 1,4-phenyldimethylene; 1,4-phenyldiethylene; 2,ethyl-1,4-phenyldimethylene; 2-methyl-1,4-phenyldimethylene; 2-methoxy-(1,4-phenyldimethylene); 2-propyl-(1,4-phenyldiethylene); and the like.

The term alkyl appearing herein for $R_2$ and $R_3$, and as a substituent on the aryl, cycloalkyl and heterocyclic group, embraces straight and branched chain alkyl radicals of 1 to 7 carbon atoms such as methyl; ethyl; n-propyl; n-butyl, n-amyl, n-hexyl; n-heptyl and the various positional isomers thereof such as isopropyl; t-butyl; sec-butyl: isoamyl, isohexyl: t-heptyl and the like.

Exemplary alkenyls as used for $R_2$ and $R_3$, and as a substituent on the aryl, cycloalkyl and heterocyclic group, include the straight and branched chain lower alkenyl groups of 2 to 7 carbons such as 1-propenyl; 2-propenyl or allyl; 1-butenyl; 2-butenyl; 1-pentenyl; 2-ethenyl; and the corresponding positional isomers such as 1 -isobutenyl; 2-isobutenyl; 2-sec-butenyl; 2-methyl-1-butenyl; 2-methyl-2-pentenyl- 2,3-dimethyl-3-hexenyl and the like.

The term alkoxy as used for $R_2$ and $R_3$, and as a substituent on the aryl, cycloalkyl and heterocyclic group, include the straight and branched chain lower alkoxy groups and the positional isomers thereof having 1 to 7 carbon atoms inclusive, for example, methoxy; ethoxy; propoxy; butoxy; n-pentoxy; n-hexoxy; isopropoxy; 2-butoxy; isobutoxy; 3-pentoxy; and the like.

The term alkenyloxy u used for $R_2$ and $R_3$ embraces the straight and branched chain lower alkenyloxy groups and the positional isomers thereof having 2 to 7 carbon atoms, for example, ethenoxy; propenoxy; butenoxy; pentenoxy; hexenoxy; isopropenoxy; isobutenoxy; sec-butenoxy; 2-methyl-1-butenoxy; 2-methyl-2-butenoxy; 2,3-dimethyl-3-butenoxy; and the like.

The term alkylenoxy appearing in the general formula comprehends, for $R_1$, $R_2$ and $R_3$, straight and branched chain alkylenoxy radicals of the formula —$OR_4$— wherein $R_4$ is an alkylene of 2 to 6 carbons, for example, 1,3-propyleneoxy; 1,4-butyleneoxy; 1,5-pentyleneoxy; and the like. Similarly, the term alkenyleneoxy comprehends, for $R_2$ and R3, radicals of the general formula —$OR_4$— wherein $R_5$ is an alkenylene of 3 to 6 carbons, such as prop-1-enyleneoxy; 1,4-but-1-enyleneoxy; 1,4-but-2-enyleneoxy; 1,5-pent-1-enyleneoxy; 1,5-hex-1-enyleneoxy; and the like.

The expressions alkylenedioxy and alkenyldioxy include the straight and branched chain radicals of the formula —$OT4O$— wherein $R_4$ is an alkylene of 2 to 6 carbons and of the formula —$OR_4O$— wherein $R_5$ s is an alkenylene of 3 to 6 carbons, such as for alkylenedioxy; propylenedioxy; butylenedioxy; pentylenedioxy; hexylenedioxy; and heptylenedioxy; and for alkenylenedioxy; prop-1-enylenedioxy; 1,4-but-1-enylenedioxy; 1,4-but-2-enylenedioxy; 1,5-pent-1-enylenedioxy; 1,6-hex-1-enylenedioxy; and 1,7-hep-1-enylenedioxy. The phrase heterocyclic ring of 5 to 8 carbons for $R_2$ and $R_3$, defines the ring formed when $R_2$ or $R_3$ is a bond, alkylene or alkenylene, and at least one of $R_2$ or $R_3$ is an alkylenoxy, alkenyleneoxy, alkylenedioxy or alkenylenedioxy with the terms as defined above.

The terms alkylene and alkenylene used when $R_2$ and $R_3$ are independently taken together to form a ring in cooperation with the carbon of the carbox-oxygen polymeric backbone, include an alkylene of 2 to 6 carbons and an alkylene of 3 to 6 carbons, such as the alkylenes: 1,2-ethylene, 1,3-propylene, 1,4-butylene, 1,5-pentylene, and 1,6-hexylene, and the alkenylenes: 1,3-prop-1-enylene, 1,4-but-1-enylene, 1,4-but-2-enylene, 1,5-pent-1-enylene, 1,6-hex-2-enylene, and 1,7-hept-2-enylene.

The terms aryloxy, aralkyleneoxy, aralkenyleneoxy, aralkylenedioxy and aralkenylenedioxy used for $R_2$ and $R_3$ include a radical of 8 to 12 carbons wherein aryloxy is ar-O—, alkyleneoxy is —$OR_4$—, alkenyleneoxy is —$OR_5$—, alkylenedioxy is —$OR_4O$—, alkenylenedioxy is —$OR_5O$—, with $R_4$ is alkylene and $R_5$ an alkenylene as defined above, and ar is phenyl. The phrase fused polycyclic ring of 8 to 12 carbons as used herein, defines a substituent in which a heterocyclic and an aryl ring have two atoms in common, for example, benzofuryl; benzopyranyl: 4,5-benz1,3-dioxepanyl, 5,6-benz-1,3-dioxepanyl; 4-5-benz-1,3-dioxolanyl; 4,5-benz-1,3-dioxyolanyl; 4,5-benz-1,3-dioxocanyl; 5,6-benz-1,3-dioxocanyl; 6,7-benz-1,3-dioxocanyl; 7,8-benz-1,3-dioxocanyl, and benz-1,3-dioxoanyl.

The term mer as used herein for polymers, copolymers and terpolymers denotes the member unit or the monomeric unit of the polymer. For example, in a homopolymer, the mer units are the same. In a copolymer, there are at least two different mer units. They can be ordered in the polymer chain in a random fashion when the original units are copolymerized in a common reaction vessel, or they can be ordered in block fashion when the polymers are combined after an initial homopolymerization of each of the different monomeric units. A terpolymer is a copolymer with at least a third mer unit.

The preferred polyorthoester for use in the practice of the present invention is poly(2,2-dioxo-trans-1,4-cyclohexane dimethylene tetrahydrofuran).

The polymer erodes by reacting with water to form non-toxic degradation products. The polymer responds to attack by water and degrades by reaction at a rate which depends on the final formulation. The primary degradation products of poly (2,2 dioxo-trans-1,4 cyclohexane dimethylene tetrahydrofuran) are dimethanol cyclohexane and gamma-butyrolactone. Degradation is retarded by base and accelerated by acid.

Advantageously, the polymer system has the ability to deliver medicament at a relatively constant rate over a prolonged period of time. The degradation period may vary from approximately several hours to months depending on the formulation parameters as well as the physical properties of the polymer selected. The degradation of the polymer occurs when the dispersion or suspension is administered to a mammalian organism and is exposed to water. With polyorthoesters such as poly(2,2-dioxo-trans-1,4-cyclohexane dimethylene tetrahydrofuran) formulations according to the present invention, it is contemplated that topical opthalmic delivery by a once-a-day eye drop is achievable.

The amount of polymer appropriate to achieve a desired controlled release effect from bioerosion will vary from formulation to formulation. The amount of polymer should not, however, be so large as to place the final formulation in solid form, taking into account molecular weight reductions achievable by heating or by polymer synthesis, and also taking into account contributions to flowability by addition of plasticizers. Where molecular weight reductions are undertaken, generally reductions to a molecular weight of about 2,000 to about 4,000 are believed appropriate, particularly for poly (2,2-dioxo-trans-1,4-cyclohexane dimethylene tetrahydrofuran).

A polymer is essentially bioerodible when formulated so that it mainly degrades by reaction with water, enzymes or other biological materials encountered upon administration to the body of a mammalian organism.

Formulations of the present invention should have a viscosity that is suited for the selected route of administration. Generally, the viscosity ranges for topical opthalmic administration will be from about 1,000 to about 100,000 cps. Approximately 5,000 to 30,000 cps is an advantageous viscosity range for ophthalmic administration in drop form. For administration in ribbon form, the viscosity is preferably from about 40,000 to about 100,000 cps. For parenteral administration the formulation preferably has a viscosity suitable for injection through an 18 guage, or smaller, needle at room temperature (about 20° C.).

When packaged for delivery after a longer shelf life or storage time, standard or other suitable preservatives may be added to the formulations.

The controlled release systems of the present invention are intended to release a drug or other medicament. Medicaments—substances used in treating or ameliorating a disease or medical condition—including drugs intended to therapeutically treat a mammalian organism, e.g., human, will typically be incorporated in the controlled release drug delivery system of this invention in therapeutically active amounts comparable to amounts administered in other dosage forms, usually, in amounts ranging from about 0.005% to about 20% by weight, and preferably from about 0.01% to about 10% by weight, based on the total weight of the formulation. Thus, for example, from about 0.01% to about 1% by weight of the anti-inflammatory steroid fluorometholone can be administered in this manner.

An illustrative but by no means exhaustive listing of such medicaments includes demulcents (for relief of "dry eye"), vasoconstrictors, antibiotics, antivirals, steroids, amino-substituted steroids, steroidal and non-steroidal anti-inflammatory agents, peptides, polypeptides, cardiotonics, antihypertensives, antiallergics, alpha- and beta-adrenergic blocking agents, ophthalmic medicaments such as anticataract agents, antiglaucoma agents and ophthalmic antiinflammatory agents, ophthalmic lubricating agents, ophthalmic topical or regional anesthetic agents, and the like.

Specific medicaments believed suitable for use in the present invention include drugs such as idoxuridine, carbachol, bethanechol, timolol, atenolol, labetolol, metoprolol, nadolol, oxprenolol, pindolol, sotalol, betaxolol, acebutolol, alprenolol, levobunolol, p-aminoclonidine, dipivefrin, epinephrine, phenylephrine, phospholine, aceclidine, demecarium, cyclopentolate, homatropine, scopolamine, pilocarpine, ethacrynic acid, furosemide, amiloride, bacitracin, neomycin, polymyxin, polymyxin B, gramicidin, gentamycin, penicillins, erythromycin, sulfacetamide, tobramycin, trospectomycin, vancomycin, ciprofloxacin, perfloxacin, olfloxacin, enoxacin, naphazoline hydrochloride, clindamycin, isofluorophate, fluorometholone, dexamethasone, hydrocortisone, fluorocinolone, medrysone, methylprednisolone, fluticasone propionate, betamethasone, estradiol, ibuprofen, diclofenac, flurbiprofen, naproxen, esters of ibuprofen, flurbiprofen, naproxen, ketorolac, suprofen, interferons, cromolyn, gancyclovir, aminozolamide, all trans-retinoic acid (Vitamin A) and the nontoxic, pharmaceutically acceptable salts thereof. Pro-drug counterparts are also within the scope of the present invention.

Topical or regional anesthetic agents include ones used during ophthalmic surgery or other ophthalmic procedures, such as lidocaine, cocaine, benoxinate, dibucaine, proparacaine, tetracaine, etidocaine, procaine, hexylcaine, bupivacaine, mepivacaine, prilocaine, chloroprocaine, benzocaine, tetracaine, and the like, as well as their acid forms.

The term "drug" as comprehended by active agent, broadly includes physiologically or pharmacologically active substances for producing a localized or systemic effect or effects in mammals including humans and primates, avians, valuable domestic household, sport or farm animals such as sheep, goat, cattle, horses, etc., or for administering to laboratory animals such as mice, rats and guinea pigs. That is, the drug delivery system of the present invention can be used for administering drugs that are active at a point in near relation to the delivery system, or, for administering drugs which will produce a response at a site remote from the point of application of the drug delivery system. The drugs that may be administered include inorganic and organic drugs without limitation, are those drugs that can be transported across a vessel, for example, drugs acting on the central nervous system such as hypnotics and sedatives, mixtures thereof such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and a bromo-isovaleryl urea; and hypnotic and sedative urethanes and disulfanes; narcotic antagonists such as naloxone and cyclazocine; psychic energizers such as isocarboxazid, nialamide, phenelzine, imipramine, tranylcypromine and paragylene; tranquilizers such as chloropromazine, promazine, fluphenazine, reserpine, deserpidine; meprobamate and benzodiazepines such as chlordiazepoxide; anticonvulsants such as primidone, diphenylhydantoin, ethyltoin, phenetruide and ethosuximide; muscle relaxants and anti-parkinson agents such as mephenesin, methocarbomal, trihexylphenidyl, biperiden and levo-dopa, also known as L-dopa and L-β-3-4dihydroxyphenylalanine; analgesics such as morphine, codeine, meperidine and nalorphine, antipyretics and anti-inflammatory agents such as aspirin, salicylamide and sodium salicylamide; local anesthetics such as procaine, lidocaine, naepaine, piperocaine, tetracaine, and dibucane: antispasmodics and antiulcer agents such as atropine, scopolamine, methscopolamine, oxyphenonium, papaverine and prostaglandins such as $PGE_1$, $PGE_2$, $PGF_{1a}$, $PGF_{2a}$, and PGA; anti-microbials such as penicillin, tetracycline, oxytetracycline, chlortetracycline, and chloramphenicol; sulfonamides; anti-malarials such as 4-aminoquinolines, 8-aminoquinolines and pyrimethamine; antivirals including idoxuridine, hormonal agents such as prednisolone, prednisolone acetate, cortisone, cortisol and triamcinolone; androgenic steroids, for example methyltestosterone and fluoxymesterone; estrogenic steroids, for example, 17 β-estradiol and ethinyl estradiol; progestational steroids, for example, 17 α-hydroxyprogesterone acetate, 19-nor-progesterone, norethindrone and progesterone; sympathomimetic drugs such as epinephrine, amphetamine, ephedrine, and norepinephrine; cardiovascular drugs, for example, procainamide, amyl nitrite, nitroglycerin, dipyridamole, sodium nitrate, and mannitol nitrate; diuretics, for example, chlorothiazide, and flumethiazide; antiparasitic agents such as bephenium hydroxynaphthoate, dichlorophen, dapsone and enitabes; neoplastic agents such as mechlorethamine, uracil mustard, 5-fluorouracil, 6-thioguanine, and procarbazine; hypoglycemic drugs such as insulin, isophane insulin suspension, protamine zinc insulin suspension, globin zinc insulin, extended insulin zinc suspension, and other like insulins derived from animal and synthetic origin including tolbutamide, acetohexamide, tolazamide, and chlorpropamide; nutritional agents, for example vitamins such as ascorbic acid, essential amino acids, essential elements such as iron, and essential fats; ophthalmic drugs such as pilocarpine base, pilocarpine hydrochloride, pilocarpine nitrate, eserine, eserine salicylate, atropine sulfate, homatropine, and eucatropine, levobunolol, petaxolol, timolol and proteins or peptides such as human epidermal growth factor (hEGF), aFGF, bFGF, IL-lra, TGF-β and gamma-interferon. The above drugs are further described in "The Pharmacological Basis of Therapeutics," edited by Goodman and Gilman, published by The Macmillan Company.

Of the aforementioned drugs, adrenocorticotrophic hormone, insulin, vitamins, especially vitamins $B_{12}$, steroids, e.g., testosterone, progesterone and triamcinolone, narcotic antagonists, e.g., naltrexone, cyclazocine and naloxone, antibiotics, e.g., tobramycin, anticancer drugs, e.g., cyclophosphamide, doxorubicin and cisplatin, antihypertensive drugs and proteins are especially contemplated in the practice of the present invention.

Another group of drugs are also especially contemplated in the practice of the present invention. Those drugs are the $C_{20}$ through $C_{26}$ amino substituted steroids of the following formula XI structure as set forth in WO 97101706, which is hereby incorporated by reference in its entirety, especially those which exhibit antioxidant functions:

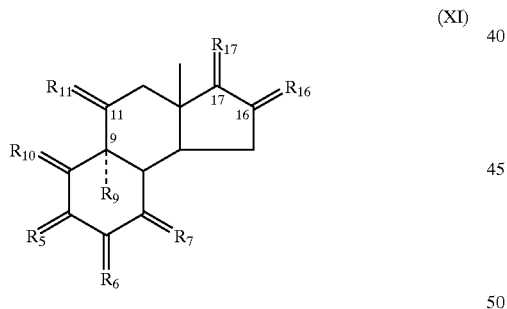

(XI)

where:
(A-I) $R_6$ is $\alpha$-$R_{61}$:$\beta$-$R_{62}$, $R_{10}$ is $\alpha$-$R_{101}$:$\beta$-$R_{102}$ and $R_7$ is $\alpha$-H:$\beta$-H, where one of $R_{61}$ and $R_{62}$ is —H, and the other is —H, —F, or $C_1$-$C_3$ alkyl, $R_{102}$ is —$CH_3$, $R_{101}$, and $R_5$ taken together are —$(CH_2)_2$—C(—$R_{33}$)—CH= or —CH—CH—CO—CH=, where R33 is =O or $\alpha$-H:$\beta$-$OR_{34}$ or $\alpha$-$OR_{34}$:$\beta$-H, where $R_{34}$ is —H, —P(=O)(OH)$_2$, —CO—$CH_3$, —CO—$C_2H_5$, —CO—$C_6H_5$, —CO—O—$CH_3$ or —CO—O—$C_2H_5$;
(A-II) $R_5$ is $\alpha$-$R_{53}$:$\beta$-$R_{54}$, $R_6$ is $\alpha$-$R_{63}$:$\beta$-$R_{64}$:$R_{10}$ is $\alpha$-$R_{103}$:$\beta$-$R_{104}$ and $R_7$ is $\alpha$-H:$\beta$-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together are —$(CH_2)_2$—C(H)(OH)—$CH_2$— or —$(CH_2)$—C[H][OP(=O)—(OH)$_2$]—$CH_2$—;
(A-III) $R_{10}$ and $R_5$ taken together are =CH—CH=C(OR$_3$)—CH= where $R_3$ is —H, —P(—O)(OH)$_2$, $C_1$-$C_3$ alkyl, —CO—H, $C_2$-$C_4$ alkanoyl or benzyl $R_6$ is $\alpha$-$R_{65}$:$\beta$-$R_{66}$ where one of $R_{65}$ and $R_{66}$ is —H, and the other is —H, —F, or $C_1$-$C_3$ alkyl and $R_7$ is $\alpha$-H:$\beta$-H;
(A-IV) $R_5$ is $\alpha$-$R_{57}$:$\beta$-$R_{58}$, $R_6$ is $\alpha$-$R_{67}$:$\beta$-$R_{68}$, $R_7$ is $\alpha$-H:$\beta$-H and $R_{10}$ is $\alpha$-$R_{107}$,$\beta$-$R_{108}$, where one of $R_{57}$ and $R_{58}$ is —H, $R_{107}$ and the other of $R_{57}$ and $R_{58}$ taken together are —$(CH_2)_2$—C(=$R_{33}$)—$CH_2$, where $R_{33}$ is as defined above, $R_{108}$ is —$CH_3$, where one of $R_{67}$ and $R_{68}$ is —H and the other is —H, —F, or $C_1$-$C_3$ alkyl;
(A-V) $R_6$ is $R_{69}$:$R_{610}$, $R_7$ is $R_{79}$:$R_{710}$, $R_{10}$ is $\alpha$-$R_{109}R_{1010}$, where one of $R_{69}$ and $R_{610}$ is —H and the other taken together with one of $R_{79}$ and $R_{710}$ forms a second bond between $C_6$ and $C_7$, ad the other of $R_{79}$ and $R_{710}$ is —H, $R_{1010}$ is —$CH_3$, $R_{109}$ and $R_5$ taken together are —$(CH_2)_2$—C(=$R_{33}$)—CH= or —CH=CH—CO—CH=, where $R_{33}$ is as defined above where:
(C-I) $R_{11}$ is $\alpha$-$R_{111}$:$\beta$-$R_{112}$, where one of $R_{111}$ and $R_{112}$ is taken together with $R_9$ to form a second bond between $C_9$ and $C_{11}$ and the other of $R_{111}$ and $R_{112}$ is —H;
(C-II) $R_9$ is —Cl and $R_{11}$ is =O or $\alpha$-H:$\beta$-$R_{114}$ where $R_{114}$ is —Cl or —OH;
(C-III) $R_9$ is —H or —F and $R_{11}$ is =O or $\alpha$-$R_{115}$:$\beta$-$R_{116}$, where one of $R_{115}$ and $R_{116}$ is —H, and the other of $R_{115}$ and $R_{116}$ is —H, —OH or $C_1$-$C_{12}$ alkoxy;
(C-IV) $R_9$ is —H or —F and $R_{11}$ is $\alpha$-O—CO—$R_{117}$:$\beta$-H, where $R_{117}$ is
(A) $C_1$-$C_3$ alkyl,
(B) $C_1$-$C_{12}$ alkoxy,
(C) furanyl,
(D) —$NR_{122}R123$, where one of $R_{122}$ and $R_{123}$ is —H, methyl or ethyl and the other is —H, $C_1$-$C_4$ alkyl or phenyl,
(E) —$X_3$—$X_1$, where $X_3$ is —O— or a valence bond, where $X_1$ is phenyl optionally substituted with 1 through 2 —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl, 1-hexamethylenimino-, 1-hexamethylenimino-, $C_2$-$C_4$ acylamino and —NH—CHO or with 1 —F or —$CF_3$; where:
(D-I) $R_{16}$ is $R_{161}$:R162 and $R_{17}$ is $R_{171}$:$R_{172}$, where one of $R_{161}$ and $R_{162}$ is —H or —$CH_3$ and the other taken together with one of $R_{171}$, and $R_{172}$ forms a second bond between $C_{16}$ and $C_{17}$, and the other of $R_{171}$ and $R_{172}$ is —C(=Z)—(CH$_2$)$_n$—$NR_{21}R_{210}$, where Z is =O, =$CH_2$ or $R_{179}$:—H where $R_{179}$ is —H or —$CH_3$, where n is 0 through 6, where
(A) $R_{21}$ is
(1) —(CH$_2$)$_m$—$NR_{211}$—$X_2$, where m is 2, 3 or 4, where $R_{211}$ is —H or $C_1$-$C_3$ alkyl, where $X_2$ is:
[A]
(a) pyridin-2-, 3- or 4-yl or the N-oxide thereof optionally substituted by 1 or 2 $R_{212}$, being the same or different, where $R_{212}$ is
(i) —F,
(ii) —Cl,
(iii) —Br,
(iv) $C_1$-$C_5$ alkyl,
(v) —$CH_2$—CH=$CH_2$,
(vi) —$X_1$, where $X_1$ is as defined above,
(vii) —$NR_{213}R_{213}$ where the $R_{213}$'s are the same or different and are —H, $C_1$-$C_3$ alkyl or —$CH_2$—CH=$CH_2$, (viiiα) *CH$_2$—(CH$_2$)$_q$—CH$_2$N*— where the atoms marked with an asterisk (*) are bonded to each other resulting in the formation of a ring, where q is 1 through 5, (viiiβ) *CH$_2$—CH$_2$—(CH$_2$)$_c$—G—(CH$_2$)$_d$—CH$_2$—CH$_2$—N*— where the atoms marked with an asterisk (*) are bonded to each other resulting in the formation of a ring, where G is —O—, —S—, —SO—, —SO$_2$ or —NHR$_{214}$, where R$_{214}$ is —H. C$_1$–C$_3$ alkyl, or X$_1$ as defined above, where c and d are the same or different and are 0 through 2 with the proviso that the total number of ring carbon atoms is 4, 5 or 6 [a]

(ix) 3-pyrrolin-1-yl, [b]

(x) pyrrol-1-yl optionally substituted with C$_1$–C$_3$ alkyl, [c]

(xi) piperidin-1-yl optionally substituted with 1 or 2 C$_1$–C$_3$ alkyl, [d]

(xii) 1,2,3,6-tetrahydro-pyridin-1-yl, [e]

(xiii) 1-hexamethyleneimino containing a 3- or 4-double bond or 3- and 5-double bonds, [f]

(xiv) 1,4-dihydro-1-pyridinyl substituted in the 4 position by two C$_1$–C$_3$ alkyl being the same or different, [g]

(xv) —OH, (xvi) C$_1$–C$_3$ alkoxy, (xvii) —NR$_{217}$—(CH$_2$)$_e$—Q where Q is 2-pyridinyl where R$_{217}$ is —H or C$_1$–C$_3$ alkyl and e is 0 through 3 [i]

(xviii) pyridin-2-, 3- or 4-yl, (b) 1,3,5-triazin-4-yl or the N-oxide thereof optionally substituted at the 2- and/or 6-position with R$_{212}$ 1 is as defined above, (4)

(c) pyrimidin-4-yl or the N-oxide thereof optionally substituted at the 2- and/or 6-position with R$_{212}$ is as defined above, (5)

(d) pyrimidin-2-yl optionally substituted at 4- and/or 6-position with 1 or 2 R$_{212}$ as is defined above, (6)

(e) pyrazin-2-yl optionally substituted with 1 or 2 R$_{212}$ as is defined above, (7)

(f) imidazol-2-yl optionally substituted in the 1 position with C$_1$–C$_3$ alkyl or —X$_1$, where X$_1$ is as defined above, and further optionally substituted with 1 or 2 R$_{212}$ as defined above, (8)

(g) 1,1,4-triazol-1-yl optionally substitute in the 1 position with C$_1$–C$_3$ alkyl or —X$_1$, where X$_1$ is as defined above, and further optionally substituted with R$_{212}$ as defined above, (9)

(h) imidazol-4- or 5-yl optionally substituted in the 1-position with C$_1$–C$_3$ alkyl or —X$_1$, where X$_1$ is as defined above, and further optionally substituted with 1 or 2 R$_{212}$ as defined above, (10)

(i) benzo[b][thien-2-yl, (12a)

(j) indol-2-yl, (12b)

(k) benzo[b]thiazol-2-yl, (12c)

(l) benzimidazol-2-yl, (12d)

(m) 4-[2-[4-[2,6-bis(1-pyrrolidinyl)-4-pyrimidinyl]-1-piperazinyl]ethyl]-piperazinyl, (13)

(n) 1,2,4-triazin-3-yl optionally substituted at the 5- and/or 6-position with R$_{212}$ is as defined above, (14)

(2) (1-piperazinyl)-(C$_2$–C$_4$)alkyl optionally substituted in the 4-position with —X$_1$ or —X$_2$ as defined above, [B]

(3) —X$_2$, as defined above, [O]

(4) —(CH$_2$)$_m$—X$_4$ where m is as defined above and where X$_4$ is (a) —O—CH$_2$CH$_2$—Y, where Y is C$_1$–C$_3$ alkylamino, di(C$_1$–C$_3$)alkylamino where the alkyl groups are the same or different, C$_3$–C$_6$ alkyleneimino, optionally substituted with 1 or 2 C$_1$–C$_3$ alkyl, (b) —NR$_{220}$CH$_2$CH$_2$—Y, where R$_{220}$ is —H or C$_1$–C$_3$ alkyl and Y is as defined above, (c) —(CH$_2$)$_g$—N(R$_{220}$)—X$_2$, where g is 2, 3 or 4, and where R$_{220}$ and X$_2$ are as defined above, [H]

(5) —(CH$_2$)$_m$NR$_{222}$R$_{223}$, where R$_{222}$ is —H or C$_1$–C$_3$ alkyl and R$_{2223}$ is —X$_1$ or —X$_2$ as defined above, or R$_{222}$ and R$_{223}$ are taken together with the attached nitrogen atom to form a saturated mono-nitrogen C$_3$–C$_6$ heterocyclic ring and where m is as defined above, [I]

(6) —(CHCH$_3$)$_b$—(CH$_2$)$_f$R$_{224}$, where b is 0 and f is 1 through 3 or b is one and f is 0 through 3, where R$_{244}$ is phenyl substituted with 1 through 3 —OH, C$_1$–C$_3$ alkoxy, —NR$_{225}$R$_{226}$ where R$_{225}$ and R$_{226}$ are the same or different and are —H, C$_1$–C$_3$ alkyl or are taken together with the attached nitrogen atom to form a C$_4$–C$_7$ cyclicamino ring, [J]

(7) —(CH$_2$)$_i$—X$_2$, where i is 1 through 4 and X$_2$ is as defined above, [K]

(8) (1-piperazinyl)acetyl substituted in the 4-position by X$_2$ where X$_2$ is as defined above, [L]

(9) (1-piperazinyl)carbonylmethyl substituted in the 4-position by —X$_2$ where X$_2$ is as defined above, and [M]

(B) R$_{210}$ is (1) —H, (2) C$_1$–C$_3$ alkyl, (3) C$_5$–C$_7$ cycloalkyl, (4) —(CH$_2$)$_m$—NR$_{211}$—X$_2$, where m, R$_{211}$ and X$_2$ are as defined above, [A]

(5) (1-piperazinyl)-(C$_2$–C$_4$)alkyl optionally substituted in the 4-position with —X$_1$ or —X$_2$ as defined above, [B]

(6) —(CH$_2$)$_m$—X$_4$, where m and X$_4$ are as defined above, [H]

(7) —(CH$_2$)$_m$—NR$_{222}$R$_{223}$, where m, R$_{222}$ and R$_{223}$ are as defined above, [I]

(8) —(CHCH$_3$)$_b$—(CH$_2$)$_f$R$_{224}$, where b, f and R$_{224}$ are as defined above, [J]

(C) R$_{21}$ and R$_{210}$ are taken together with the attached nitrogen atom to form a heterocyclic ring selected from the group consisting of (1) 2-(carboxy)-1-pyrrolidinyl optionally as the C$_1$–C$_3$ alkyl ester or as a pharmaceutically acceptable salt, [C-1]

(2) 2-(carboxy)-1-piperidinyl optionally as the C$_1$–C$_3$ alkyl ester or as a pharmaceutically acceptable salt [C-2]

(3) 2-(carboxy)-1-hexamethyleneimino optionally as the C$_1$–C$_3$ alkyl ester or as a pharmaceutically acceptable salt, [C-3]

(4) 2-(carboxy)-1-heptamethylene-imino optionally as the C$_1$–C$_3$ alkyl ester or as a pharmaceutically acceptable salt, [C-4]

(5) 1-piperazinyl substituted in the 4-position with R$_{228}$—CO—(CH$_2$)$_j$ where R$_{228}$ is —X$_1$, —NR$_{229}$X$_1$ and 2-furanyl, where R$_{229}$ is —H or C$_1$–C$_3$ alkyl, where j is 0 through 3 and X$_1$ is as defined above, [D]

(6) 1-piperazinyl substituted in the 4-position with X$_2$—(CH$_2$)$_j$— where X$_2$ and j are defined above, [E]

(7) 1-piperazinyl substituted in the 4-position with $X_1$—$(CH_2)j$—, where $X_1$ and j are as defined above, [F]
(8) 4-hydroxy-1-piperidinyl substituted in the 4-position with $X_1$ as defined above, [G]
(9) 1-piperazinyl substituted in the 4-position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is —CH—$(CH_2)_p$—$NR_{21}R_{210}$, where p is 1 or 2, where $R_{21}$ and $R_{210}$ are as defined above.

(D-III) $R_{16}$ is $\alpha$-$R_{6165}$:$\beta$-$R_{166}$ and $R_{17}$ is $\alpha$-$R_{175}$:$\beta$-$R_{176}$, where $R_{165}$ is —H, , —OH, —F or —$CH_3$ and $R_{166}$ is —H, —OH, —F, or —$CH_3$, with the proviso that is at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is as defined above, and where $R_{176}$ is —C(=Z)—$(CH_2)n$—$NR_{21}R_{210}$, where Z, n, $R_{21}$ and $R_{210}$ are as defined above;

(D-IV) the 16,17-acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, $R_{21}$ and $R_{210}$ are as defined above;

and pharmaceutically acceptable salts thereof,
and hydrates and solvates thereof;
with the following overall provisos that;

(I) one of $R_{161}$ or $R_{162}$ is taken together with one of $R_7$, or $R_{172}$ to form a second bond between $C_{16}$ and $C_{17}$, only when $R_{10}$ is $\alpha$-$R_{10}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (II) $R_{17}$ is —CH—$(CH_2)_p$—$NR_{21}R_{210}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (III) $R_5$ and $R_{10}$ taken together are =CH—CH=C$(OR_3)$—CH=, only when $R_{17}$ is $\alpha$-$R_{175}$:$\beta$-$R_176$ or the 16,17-acetonide of a compound where $R_{16}$ is $\alpha$-OH:$\beta$-H and $R_{17}$ is $\alpha$-OH:$\beta$-C(=Z)—$(CH_2)_n$—$NR_{21}R_{210}$, and (IV) $R_5$ is $\alpha$-$R_{57}$:$\beta$-$R_{57}$, only when $R_{17}$ is $\alpha$-$R_7$:$\beta$-$R_{176}$ or $\alpha$OH:$\beta$-C—(=Z)—$(CH_2)_nNR_{21}R_{210}$, or the 16,17-acetonide thereof.

More preferred are the $C_{12}$ aminosteroids of formula XI, especially those which inhibit lipid peroxidation. Most preferred are the 21-[4-(substituted-4-pyrimidinyl)-1-piperazinyl]-steroids, such as U-74006 (21-[4-(2,6-dipyrrolidinyl-4-pyrimidinyl)-1-piperazinyl]-16$\alpha$-methylpregna-1,4,9(11)-triene-3,20-dione, and the 21-[4-(substituted-2-pyridinyl)-1-piperazinyl]-steroids, such as U-74500 (21-[4-[5,6-bis(diethylamino)-2-pyridinyl]-1piperazinyl]-16$\alpha$-methylpregna-1,4,9(11)-triene-3,20-dione and U-75412 (21-[4-(3-ethylamino-2-pyridinyl)-1-piperazinyl]-16$\alpha$-methylpregna-1,4,9(11)-triene-3,20-dione, all, when in the unformulated state, preferably as a solid, preferably crystalline, preferably relatively non-hygroscopic and pharmaceutically acceptable salts, such as the methanesulfonate salt of U74006 (U-74006F), the hydrochloride of U-74500 (U-74500A), and the hydrochloride or maleic acid salt of U-75412 (U-75412A and U-75412E, resp.)

The drugs or other medicaments also can be in various forms such as uncharged molecules, components of molecular complexes, pharmacologically acceptable salts such as hydrochloride, hydrobromide, sulfate, laureates, palmatates, phosphate, nitrate, borate, acetate, maleate, tartrate, oleates, and salicylates. For acidic drugs, salts of metals, amines, or organic cations, for example quaternary ammonium can be employed. Furthermore, simple derivatives of the drug such as esters, ethers, and amides which have solubility characteristics that are suitable for the purpose of the invention may be used. Also, a medicament or drug that is water insoluble can be used in a form that is a water soluble derivative thereof to effectively serve as a solute, and on its release from the device, it is converted by enzymes, hydrolyzed by body pH, or metabolic processes to the original form or to a biologically active form.

The term "pharmaceutically acceptable salt" refers to those salts of the parent compound that do not significantly or adversely affect the pharmaceutical properties (e.g., toxicity, efficacy, etc.) of the parent compound. Pharmaceutically acceptable salt administrable by means of the dispersions or suspensions of this invention include, for example, chloride, iodide, bromide, hydrochloride, acetate, nitrate, stearate, pamoate, phosphate, borate and sulfate salts. It is sometimes desirable to use an appropriate salt form of the drug that increases the water solubility or polar characteristics of the free drug.

Applications disclosed by Choi et al dictate that the free base form of the drug be administered because the acid forms are very water soluble and act as autocatalytic agents which degrade the polymer by acid hydrolysis. With the present invention, on the other hand, use of either the acid form or the free base form of the drug can be undertaken. The acid form is oftentimes more stable than the free base form. When acid forms of drugs are employed, addition of small amounts of a buffer (such as 0.2% $NaH_2PO_4$, by weight based on the final formulation) may be desirable.

The present invention is also particularly advantageous for use with water soluble drugs especially when they are suspended or dissolved in the bioerodible polymer. Generally they will not readily diffuse out of the polymer matrix which will thus need to bioerode for delivery of the medicament.

A controlled release drug delivery system of the present invention can be made by a variety of techniques. Basic determinations that should be made include the selection of the bioerodible polymer, selection of the plasticizer or configuration of plasticizers, and selection of the medicament. Desired system viscosity, giving due attention to the route of administration, will need to be taken into account, and will affect the amount and selection of plasticizer to be used.

The choice of the constituents and order of combining the constituents can vary, and certain choices or orders can be more advantageous for certain purposes. For example, when using medicaments that can be unstable at elevated temperatures, plasticizer may be used in amounts and at a time which ensures sufficient flowability or a lower molecular weight polymer may be used so that lower temperatures might be employed when the medicament is added.

In selecting plasticizers, low molecular weight polyethylene glycol (PEG) or polypropylene glycol (PPG) appear particularly appropriate especially in connection with the preferred poly(2,2-dioxy-trans-1,4-cyclohexane dimethylene tetrahydrofuran) polymer. The molecular weight of the PEG or PPG is preferably between about 200 to about 400. The PEG more preferably has a molecular weight of about 300. The low molecular weight PEG or PPG acts as a plasticizer and allows the polymer to be more easily and more uniformly dispersed in the final formulation. Cetyl alcohol is also contemplated as a plasticizer, either alone or more preferably along with polyethylene glycol or glycerin. The plasticizer may comprise about 5–40% (more preferably about 10% to about 30%) by weight cetyl alcohol, based on the weight of the plasticized polymer, and about 1–5% by weight glycerin, based on the weight of the plasticized polymer (excluding medicament).

The amount of plasticizer employed should be sufficient to make the polymer flowable, without adversely interfering with the control release characteristics of the polymer. The total amount of plasticizer will generally be about 5% to about 70% by weight of the total weight of the flowable bioerodible delivery system, made up of bioerodible polymer and plasticizer (excluding medicament), more preferably, about 5% to about 40% and for some formulation preferably about 10% to about 30% by weight.

To more uniformly entrap maximum amounts of medicament in the essentially bioerodible delivery system, that medicament is best mixed with the plasticized flowable bioerodible polymer after it has been plasticized. The mixing can desirably involve active agitation, e.g. stirring, and might be enhanced by heating. Certain medicaments can be dissolved readily by the essentially bioerodible polymer. Other will be dispersed, with steps such as stirring being undertaken to establish a basically uniform dispersion (i.e., a suspension), Partial dissolution and partial dispersion can also be realized depending upon compatibility of the medicament with the polymer and plasticizer.

In most instances it will be desirable at some stage to heat the plasticized essentially bioerodible polymer to render it more flowable. Advantageously, that might be undertaken at the stage of adding the medicament. If the initial heating occurred without medicament having first been added, heat might advantageously be supplied when the medicament is later added.

Heat can also be advantageously employed to bring viscosities into a desired range. In this regard, high molecular weight polyorthoester materials have been subjected to temperatures of 140° C. to 180° C. for 30 minutes to several days to reduce molecular weight and provide viscosities of 100,000 cps and lower when plasticized. The temperature and duration of heating to achieve the desired viscosity can depend upon the selection of plasticizers, polymer molecular weight, and concentrations of the polymer alternatively, a lower molecular weight polymer may be used.

When it is preferred that formulations of the present invention be stable over a period of several months or longer, standard or other preservatives can, if desired, be added at any appropriate stage in preparation of the formulations. However, preservative-free packaging in single or limited dose non-reusable containers is also contemplated. Any container used here should be protected from water vapor transport therethrough by overwrapping with an aluminum container since water is reactive with the polymer.

When preservatives are to be employed, typical preservatives readily known to those skilled in the art may be determined from any pharmaceutical compounding reference text such as *Remingtons Pharmaceutical Sciences*. Such preservative include chlorobutanol, methyl paraben, propyl paraben, and the like, at levels typically ranging from about 0.001 to about 0.5% by weight based on the weight of the final formulation.

Throughout the formulation process, exposure to water or water vapor is desirably minimized or altogether avoided.

Although in certain circumstances, the entire process for preparing a controlled drug delivery system of the present invention might be conducted at room temperature. As mentioned above the use of heat can be advantageously in the manufacturing process, perhaps at the time of addition of each component. The amount of heat will generally be dependent on the polymer selected since different polymers have different melting points. Temperatures used in each step are preferably only slightly above the softening temperatures for the combined ingredients. The final heating step, i.e., once all the components are present, if used, will typically produce a temperature in the range of about 50° C. to 80° C.

Medicament is added to plasticized bioerodible polymer at a temperature compatible with the heat stability of the medicament. Ordinarily, medicament will be added at a temperature of about 20° C. to about 80° C., more preferably about 40° C. to about 80° C.

Suitable carriers for injectable formulation are well known to persons skilled in the art, e.g., citrate buffer, borate buffer, phosphate buffer and others. Other additives which may be desirably added to parenteral formulations include sodium chloride, sodium sulfite, disodium edetate and benzyl alcohol. Suitable adjuvants for intramuscular formulations are those well known to persons skilled in the art such as polysorbate 80, methyl cellulose, and other demulcents. Other additives desirably added to intramuscular formulations include sodium chloride and sodium bisulfite. Finally, formulations suitable for oral administration will include liquid formulations (solutions, suspension, elixirs, and the like) containing additives and adjuvants well known to persons skilled in the art. Suitable adjuvants may be used as carriers to provide wetability and stability. Other additives, including sodium edetate, flavoring agents and colorants may be employed if desired. Some amounts of acid or base can be used to regulate the release rate of the medicament by controlling the erosion rate through speeding up or slowing down the rate of hydrolysis. Any or all of the foregoing might be employed in certain formulations according to the present invention so long as the basic characteristics of the system previously described are maintained.

Conventional encapsulation materials may be used to encapsulate systems of the present invention to provide an encapsulated formulation suitable for oral administration. Alternatively the present invention may be formulated as a liquid, preferably a viscous liquid, for oral administration.

The following examples are set forth to illustrate the spirit of the present invention. They are not to be construed so as to limit the scope of the invention, as various ways of implementing the present invention will be readily apparent to those skilled in the subject art.

EXAMPLES 1–15

In Examples 1–15 the polymer is poly (2,2-dioxy-trans-1,4cyclohexane dimethylene tetrahydrofuran) having a molecular weight of approximately 17,000 and being in extremely viscous liquid form. The polymer along with the plasticizer, e.g., polyethylene glycol and cetyl alcohol and/or glycerin, is weighed into a small vial containing a magnetic stir bar in a dry environment. The vial is capped, filled with nitrogen, and the contents are heated while continuously stirring for 0.5 to 8 hours at a temperature from 140° to 180° C. under a vacuum of about 1 to 5 mm Hg. When the heat is removed, the mixture is allowed to cool to room temperature with continuous stirring. After cooling to room temperature, the medicament is added, the vial is heated for 30 to 120 minutes at 40° to 80° C. under a vacuum to about 1–5 mm Hg while continuously stirring. After mixing the vial is allowed to cool to room temperature.

Precautions are taken to minimize exposure of the polymer to air by doing all the formulation work in nitrogen purged capped vials and working in a dry box. Completed formulations are placed in unit-dose vials with a syringe and the unit dose tubes are sealed. The tubes are overwrapped in laminated foil bags to prevent water vapor transport through the plastic tubes. Sterilization of the formulation is accomplished by Co-60 radiation at a dose of 2.5 mRAD.

| Example No. | % Polymer | % PEG 300 | % Cetyl Alcohol | % Glycerol | % Proparacaine HCl |
|---|---|---|---|---|---|
| 1  | 66.5 | 28.5 |      |     | 5.0 |
| 2  | 70.0 | 29.5 |      |     | 0.5 |
| 3  | 65.3 | 27.1 |      | 7.1 | 0.5 |
| 4  | 80.0 | 19.5 |      |     | 0.5 |
| 5  | 70.0 | 29.5 |      |     | 0.5 |
| 6  | 70.0 |      | 29.5 |     | 0.5 |
| 7  | 80.0 |      | 19.5 |     | 0.5 |
| 8  | 55.0 | 10.0 | 30.0 |     | 5.0 |
| 9  | 65.0 | 20.0 | 10.0 |     | 5.0 |
| 10 | 80.0 |      | 7.5  | 7.5 | 5.0 |
| 11 | 67.5 |      | 22.5 | 5.0 | 5.0 |
| 12 | 76.5 |      | 20.0 | 3.0 | 0.5 |
| 13 | 74.5 |      | 20.0 | 5.0 | 0.5 |
| 14 | 72.5 |      | 20.0 | 7.0 | 0.5 |
| 15 | 73.5 |      | 20.0 | 6.0 | 0.5 |

EXAMPLES 16–34

In Examples 16–34, the polymer is poly (2,2-dioxy-trans-1,4-cyclohexane dimethylene tetrahydrofuran) in solid form with a molecular weight greater than 30,000. The polymer and plasticizer are weighed into a vial capped under dry nitrogen with a magnetic stirrer. The sample is heated at 140–180° C. for 2–24 hours under a vacuum of at least about 1–5 mm Hg while stirring. The vial is cooled to room temperature, the medicament and buffer, if present, are weighed in. The vial is recapped and stirred for 2 hours at a temperature of 40–80° C. under a vacuum of about 1–5 mm Hg. The formulation is cooled to room temperature, filled with a syringe into unit dose containers, sealed, and overwrapped with an aluminum laminate. The formulations were sterilized with a 2.5 MRAD dose of Co-60 radiation.

EXAMPLE 35–40

In Examples 35–40, poly (2,2-dioxy-trans-1,4 cyclohexane dimethylene tetrahydrofuran) is used as the polymer having a molecular weight of approximately 17,000 and in an extremely viscous liquid form. This polymer, along with the plasticizer, are weighed into a small vial containing a magnetic stir bar in a dry environment. The vial is capped, filled with nitrogen, and the contents are heated for 15 to 24 to 180° C. under a vacuum at about 1–5 mm Hg while stirring. When the heat is removed, the mixture is allowed to cool to room temperature with continuous string. After cooling to room temperature, the weighed amount of medicament, is added to the mixture. Then, the mixture is dissolved in 100 grams of ethanol in a sealed flask. The ethanol is stripped off using a rotorvapor under vacuum of about 1–5 mm Hg at a temperature of 30 to 40° C. Samples are filled and sterilized n stated in previous examples.

| Example No. | % Polymer | % Cetyl Alcohol | % Glycerin | % PEG-300 | % Phosphate Buffer | % Pilocarpine HCl |
|---|---|---|---|---|---|---|
| 35 | 74   | 20   | 5 |    |    | 1 |
| 36 | 73.8 | 20   | 5 |    | .2 | 1 |
| 37 | 95   |      | 5 |    |    |   |
| 38 | 95   |      | 4 |    |    | 1 |
| 39 | 64   | 25   |   | 10 |    | 1 |
| 40 | 64   | 24.5 |   |    | .2 | 1 |

The foregoing discussion of the present invention was directed primarily to preferred embodiments and practices thereof. It will be readily apparent to those skilled in the art that further changes and/or modifications in actual implementation of the concepts described herein can be made without departing from the spirit and scope of the invention as defined by the following claims.

What is claimed is:

1. A topical ophthalmic composition consisting essentially of a flowable bioerodible polymer plasticized with up to about 70%. plasticizer by weight of the plasticized polymer, and medicament carried in said polymer, wherein the composition has a viscosity formulated for administration to the eye in drop or ribbon form.

| Example No. | % Polymer | % Cetyl Alcohol | % Glycerin | % PEG 300 | % Dibasic Phosphate | % Pilocarpine Hcl | % Pilocarpine | % Fluoro metholone |
|---|---|---|---|---|---|---|---|---|
| 16 | 69   | 25 | 5   |      |    | 1 |   |    |
| 17 | 69   | 25 | 5   |      |    |   | 1 |    |
| 18 | 71   | 20 | 4   |      |    | 5 |   |    |
| 19 | 71   | 20 | 4   |      |    |   | 5 |    |
| 20 | 69.9 | 25 | 5   |      |    |   |   | .1 |
| 21 | 70.8 | 20 | 4   |      | .2 | 5 |   |    |
| 22 | 94   |    | 5   |      |    | 1 |   |    |
| 23 | 90   |    | 5   |      |    | 5 |   |    |
| 24 | 90   |    | 4.8 |      | .2 | 5 |   |    |
| 25 | 65   | 15 | 5   | 10   |    | 5 |   |    |
| 26 | 75   | 20 | 5   |      |    |   |   |    |
| 27 | 69.8 | 20 | 5   |      | .2 |   |   |    |
| 28 | 70   |    | 2   | 28   |    |   |   |    |
| 29 | 70   |    | 2   | 27   |    | 1 |   |    |
| 30 | 70   |    | 2   | 28   |    |   |   |    |
| 31 | 70   |    |     | 28   |    | 2 |   |    |
| 32 | 70   |    | 2   | 27.9 |    |   |   | .1 |
| 33 | 60   |    |     | 39   |    | 1 |   |    |
| 34 | 60   |    |     | 39.7 | .2 |   |   | .1 |

2. A topical ophthalmic composition according to claim 1, wherein the polymer is selected from the group consisting of polysaccharides, proteinaceous polymers, soluble derivatives of proteinaceous polymers, polyesters, polylactic acid polymers, polyglycolic acid polymers, poly (lactic/glycolic) copolymers and polyorthoesters.

3. A topical ophthalmic composition comprising a composition according to claim 2 wherein the plasticizer is selected from the group consisting of polyethylene glycol, ethylene glycol, polypropylene glycol, propylene glycol, glycerine, polyvinyl alcohol and cetyl alcohol.

4. A topical ophthalmic composition according to claim 3 wherein the polymer is a polyorthoester.

5. A topical opthalmic composition comprising a flowable bioerodible polyorthoester polymer plasticized with up to about 70% plasticizer by weight of the plasticized polymer, and medicament carried in said polymer, wherein the composition has a viscosity formulated for administration to the eye in drop or ribbon form.

6. A topical ophthalmic composition consisting essentially of a flowable bioerodible polymer, which breaks down by chemical decomposition upon reaction with biological materials, plasticized with up to about 70% plasticizer by weight of the plasticized polymer, and medicament carried in said polymer, wherein the composition has a viscosity formulated for administration to the eye in drop or ribbon form, and wherein the amounts of said plasticizer, said bioerodible polymer and said medicament are respectively in the ranges of about 5% to about 70% plasticizer, about 30% to about 95% bioerodible polymer, and about 0.05% to about 20% medicament.

7. A composition according to claim 4, wherein the medicament is selected from the group consisting of demulcents, anticataract agents, antiglaucoma agents, ophthalmic antiinflammatory agents, ophthalmic lubricating agents, ophthalmic topical anesthetic agents, ophthalmic regional anesthetic agents, vasoconstrictors, and agents to treat retinal diseases.

8. A sustained release medicament delivery system, comprising about 30% to about 95% of a bioerodible polymer for carrying medicament, wherein said polymer is plasticized by about 5% to about 70% cetyl alcohol.

9. A sustained release medicament delivery system according to claim 8 wherein the polymer is also plasticized by glycerin or polyethylene glycol.

10. A sustained release medicament delivery system according/to claim 8, wherein the polymer is selected from the group consisting of polysaccharides, proteinaceous polymers, soluble derivatives of proteinaceous polymers, polyesters, polylactic acid polymers, polyglycolic acid polymers, poly (lactic/glycolic) copolymers and polyorthoesters.

11. A sustained release medicament delivery system according to claim 8 wherein the polymer is a polyorthoester.

12. A sustained release medicament delivery system according to claim 11 wherein the polymer is poly (2,2 dioxo-trans-1,4 cyclohexane dimethylene tetrahydrofuran).

13. A sustained release medicament delivery system according to claim 9 wherein the glycerin or polyethylene glycol is about 1%–5% by weight of the plasticized polymer (excluding medicament).

14. A sustained release medicament delivery system according to claim 13 wherein the cetyl alcohol is present in an amount of about 5% to about 30% by weight of the plasticized polymer (excluding medicament).

15. A sustained release medicament delivery system according to claim 12, wherein the cetyl alcohol is about 10% to about 30% by weight of the plasticized polymer and glycerin is also included in about 1%–5% by weight of the plasticized polymer.

16. A sustained release medicament delivery system, comprising:
    medicament carried by a flowable bioerodible polyorthoester polymer which polymer is plasticized by about 5% to about 70% plasticizer based on the weight of polymer and plasticizer.

17. A sustained release medicament delivery system according to claim 16, wherein the plasticizer is selected from the group consisting of polyethylene glycol, ethylene glycol, polypropylene glycol, propylene glycol, glycerine, polyvinyl alcohol and cetyl alcohol.

18. A sustained release medicament delivery system according to claim 17, wherein the polymer is poly (2,2 dioxo-trans-1,4 cyclohexane dimethylene tetrahydrofuran).

19. A sustained release medicament delivery system according to claim 18 wherein the plasticizer is about 10%–30% by weight cetyl alcohol and about 1%–5% weight percent glycerin.

20. A sustained release delivery system according to claim 12, wherein the medicament is a water soluble drug and viscosity of the system is formulated for administration by injection.

21. A sustained release delivery system according to claim 8, wherein the viscosity of the system is about in the range of about 1,000 to about 55,000 cps formulated for administration to the eye in ribbon or drop form.

22. A sustained release delivery system according to claim 20 wherein the viscosity of the system provides for administration through an 18 gauge or smaller needle.

23. A sustained release delivery system according to claim 17 herein the system is formulated for oral administration.

24. A sustained release delivery system according to claim 17 wherein the medicament is formulated for injection.

25. A sustained release medicament delivery system as recited in claim 17 formulated for oral administration as a viscous liquid.

26. A sustained release medicament delivery system as recited in claim 17 formulated in capsule form for oral administration.

27. A proceed for making a sustained release medicament system, comprising:
    a) heating while mixing a bioerodible polymer, which breaks down by chemical decomposition upon reaction with biological materials, with a plasticizer for the polymer to form a flowable bioerodible polymer;
    b) cooling the plasticized, flowable, bioerodible polymer; and
    c) adding medicament to the delivery system at a temperature compatible with the heat stability of the medicament; wherein said flowable bioerodible polymer is about 5% to about 70% plasticizer based on the weight of polymer and plasticizer.

28. A process according to claim 28, wherein the medicament is added when the flowable bioerodible polymer is at a temperature of about 80° C.

29. A process according to claim 28, wherein the polymer is selected from the group consisting of polysaccharides, proteinaceous polymers, soluble derivatives of proteinaceous polymers polyesters, polylactic acid polymers, polyglycolic acid polymers, poly (lactic/glycolic) copolymers and polyorthoesters and the polymer and plasticizer are heated to a temperature between about 40° C. to 180° C.

30. Process according to claim 29, wherein the bioerodible polymer is polyorthoester plasticized with cetyl alcohol and about 1%–5% glycerine, and the mixture containing medicament is heated to a temperature between about 40° C. to 80° C.

31. A process according to claim 30 wherein the cetyl alcohol is about 30% of the plasticized polyorthoester.

32. A process according to claim 28 wherein the medicament is added during said cooling.

33. A process according to claim 27 wherein after said cooling the plasticized flowable bioerodible polymer is reheated and medicament is added during said reheating of the polymer.

34. A process for making a sustained release medicament system, comprising
   a) heating while mixing a bioerodible polymer, which breaks down by chemical decomposition upon reaction with biological materials, with a plasticizer for the polymer to form a flowable bioerodible polymer;
   b) cooling the plasticized, flowable bioerodible polymer;
   c) adding medicament to the bioerodible polymer and dissolving the polymer and medicament in a solvent;
   d) removing the solvent; wherein the flowable bioerodible polymer is about 5% to about 70% plasticizer based on the weight of polymer and plasticizer.

35. A process for therapeutic treatment of mammals comprising:
   a) providing a topical ophthalmic composition formulated with a medicament in a sustained release delivery system comprising a plasticized bioerodible polyorthoester polymer; said plasticized bioerodible polymer containing about 5% to about 70% plasticizer based on the weight of the plasticized polymer and plasticizer;
   b) delivering the formulation to the eye of a mammal in need of treatment with the medicament.

36. A process according to claim 35 wherein the plasticizer is selected from the group consisting of polyethylene glycol, ethylene glycol, polypropylene glycol, propylene glycol, glycerine, polyvinyl alcohol and cetyl alcohol.

37. A process according to claim 36 wherein the polymer is poly (2,2, dioxo-trans-1,4 cyclohexane dimethylene tetrahydrofuran).

38. A process according to claim 37, wherein the polymer is plasticized by cetyl alcohol and glycerin.

39. A topical ophthalmic composition according to claim 4 or claim 5, wherein the plasticizer comprises about 5–40% by weight cetyl alcohol, based on the weight of plasticized polymer and about 1–5% by weight percent glycerin, based on the weight of plasticized polymer.

40. A composition according to claim 39 wherein the polymer is poly (2,2 dioxo-trans-1,4 cyclohexane dimethylene tetrahydrofuran).

* * * * *